United States Patent [19]

Bolzan

[11] Patent Number: 4,697,028

[45] Date of Patent: Sep. 29, 1987

[54] PROCESS FOR PRODUCING A DISULFIDE DIMER OF EPTD

[75] Inventor: Louis F. Bolzan, Briarcliff Manor, N.Y.

[73] Assignee: Stauffer Chemical Company, Westport, Conn.

[21] Appl. No.: 809,631

[22] Filed: Dec. 16, 1985

[51] Int. Cl.$^4$ .............................................. C07F 9/38
[52] U.S. Cl. ........................................ 558/89; 568/14
[58] Field of Search ............................ 568/14; 558/89

[56] References Cited

U.S. PATENT DOCUMENTS 3,155,708 11/1964 Chupp et al. .
3,155,709 11/1964 Newallis et al. .
3,496,235 2/1970 Maier ................................... 568/14

FOREIGN PATENT DOCUMENTS 248677 12/1969 U.S.S.R. .

OTHER PUBLICATIONS

Maier, Topics in Phosphorus Chemistry, vol. 2, pp. 50–59, Interscience (1980).

Primary Examiner—Helen M. S. Sneed

[57] ABSTRACT

The invention pertains to a process for producing a disulfide dimer of hydrocarbylthiophosphonic dichloride wherein a hydrocarbylthiophosphonic dichloride is reacted with hydrogen sulfide. In the process disclosed, the reaction is conducted in the presence of a small amount of solvent which dissolves the product at high temperature and has very low solubility in the product at low temperature. In recovering the product an additional amount of solvent is added to the reaction product thereby allowing for the recovery of the product as a slurry after completion of the reaction. Optionally and preferably, a packed column is used in the process which increases the reaction rate.

8 Claims, No Drawings

PROCESS FOR PRODUCING A DISULFIDE DIMER OF EPTD

BACKGROUND OF THE INVENTION

1. Field of the Invention

This invention relates to hydrocarbylthionophosphine sulfide dimers and their preparation. In particular the invention is directed to the preparation of a disulfide dimer of ethylthiophosphonic disulfide (EPTD).

2. Related Art

It is known in the art to prepare hydrocarbylthiophosphine sulfide by the reaction of hydrogen sulfide with a hydrocarbylthiophosphonic dichloride. The known prior art methods are exemplified in "Topics in Phosphorus Chemistry", Vol. 2, pp. 50–59 (John Wiley & Son 1980) wherein a process for producing thionophosphine sulfides is disclosed comprising the reaction of an alkyl or aryl phosphonothioate dichloride with hydrogen sulfide at elevated temperatures. It is indicated that the temperature at which the reaction occurs is dependent upon the phosphonothioate dichloride used and is usually above 160° C. It is further indicated that the reaction rate is slow and requires several hours for completion but that the rate of reaction increases in the presence of a tertiary amine. Further it is stated that in such instances, where a tertiary amine is used, the reaction is usually carried in an inert solvent such as a hydrocarbon, methylene chloride or ether at temperatures ranging from 40°–150° C. which is below the melting point of the product.

In U.S. Pat. Nos. 3,155,708 and 3,155,709 there is disclosed a process for preparing hydrocarbylphosphonic phosphonodithioic acid and esters thereof. The method disclosed for making the intermediate hydrocarbyl thionophosphine sulfide in each instance was by reacting a hydrogen sulfide with hydrocarbylthionophosphonic dichloride. In the examples provided it is disclosed that the hydrocarbylthionophosphine sulfide product when formed is a solid which is recovered by being broken out of the reaction vessel.

SUMMARY OF THE INVENTION

A method of producing a disulfide of hydrocarbylthiophosphonic dichloride which allows for its easy production and recovery has been found. The process comprises the use of a solvent in the reaction and product recovery process wherein a hydrocarbylthiophosphonic dichloride is reacted with hydrogen sulfide at a temperature above 150° C. The solvent provides for the recovery of the product in slurry form.

DETAILED DESCRIPTION OF THE INVENTION

A process for producing a disulfide of hydrocarbylthiophosphonic dichloride represented by the formula

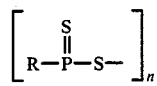

is disclosed, wherein n is a whole number, usually less than 5, and where R is a hydrocarbyl radical free of aliphatic unsaturation (i.e., free of olefinic and/or acetylenic unsaturation), as for example the various alkyl, aryl, alkaryl, aralkyl, cycloalkyl, fused carboxylic aromatic, partially and fully hydrogenated fused carboxylic aromatic radicals, each containing 1–18 carbon atoms, exemplary of which are methyl, ethyl, propyl, butyl, amyl, hexyl, heptyl, octyl, decyl, dodecyl, tetradecyl, octadecyl, cyclopentyl, cyclohexyl, cycloheptyl, methylcyclohexyl, cyclohexylmethyl, bicyclohexyl; phenyl, toly, xylyl, cumyl, dodecylphenyl, cyclohexylphenyl, benzyl, phenethyl, phenpropyl, bibenzylyl, benzylphenyl, biphenylyl, napthyl, tetrahydronaphthyl, anthracyl, phenanthryl, indanyl, indenyl, fluorenyl, etc., and the various isomeric forms thereof containing up to 18 carbon atoms. In general, it is preferred that the hydrocarbyl radical be phenyl, $C_6H_5$, or an alkyl radical containing 1–4 carbon atoms and having at least one hydrogen substituent on the alpha carbon atom (i.e., the primary and secondary alkyl radicals as exemplified by methyl, ethyl, n-propyl, n-butyl, isopropyl, isobutyl, and sec. butyl).

The hydrocarbylthionophosphine sulfide with a hydrocarbylthiophosphonic dichloride of the formula

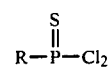

wherein R has the aforementioned significance. The reaction is accompanied by the evolution of hydrogen choride and therefore the overall chemical equation can be set forth as follows:

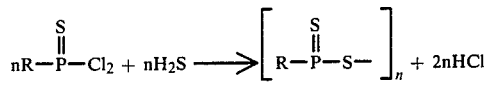

where n is a whole number usually less than 5, and wherein R is as previously stated. The hydrocarbylthionophosphine sulfide product so produced is in many instances a mixture, the component parts of which are characterized by a ratio of substituents of phosphorus to sulfur to hydrocarbyl radical R of approximately 1:2:1 and which satisfies the formula:

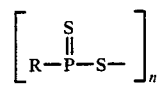

The product is predominately in the dimeric form (i.e., n=2), the other forms when present usually are the trimeric or tetrametric or higher polymeric forms.

The novel process of preparing the hydrocarbylthionophosphine sulfide is by utilizing a solvent during the reaction and recovery process which is inert to the hydrogen sulfide reactant and HCl reaction product, but which dissolves the product at a high temperature and has very low solubility in the product at low temperatures. In addition to the use of such a solvent, the process also comprises the utilization of a packed column to provide increased surface area for the hydrogen sulfide-hydrocarbylthionophosphonic dichloride reaction thereby increasing the reaction rate which would normally be lowered by the addition of a solvent if this additional precaution were not followed.

Solvents suitable for use in the practice of the invention are as detailed above and additionally are solvents which have sufficiently high boiling temperatures so as not to adversely affect the reaction temperature. The preferred solvent is toluene. During the reaction, enough solvent is added to condense and reflux solvent and any product formed back to the reactor. Amounts of from about 1-20% by weight of the total reactants and preferably 5% by weight of the reactants utilized are deemed desirable.

In this improved method of producing hydrocarbonylthionophine sulfide, which facilitates production and recovery in commercial processes, hydrogen sulfide is reacted with hydrocarbonylphosphonothioic dichloride in the presence of the solvent. The amount of solvent should be limited so that the boiling point of the reaction mixture is over 140° C., generally from 140° C.-180° C., and preferably over 160° C., at atmospheric pressure. The gases exiting the reactor consist of hydrogen chloride, hydrogen sulfide, solvent and hydrocarbonylphosphonothioic dichloride. The latter two materials are condensed by cooling and are washed back to the reactor. Preferably, the gases are passed though a packed column and the condensed liquids are returned to the top of the column.

In the absence of solvent, solids would form by the reaction in the vapor space of the reactor towards the end of the reaction (Example I). Potentially, a reactor vent could, as a result, become obstructed, which can be hazardous. When some solvent is present, it dissolves these solids and returns them to the reaction liquid (Example I). However, the addition of excess amounts of solvent during the reaction process would lower the reaction temperature below the 140° C. required for the process.

The reaction is sufficiently complete when no further HCl evolution is detected; then the flow of hydrogen sulfide is stopped. Thereafter, additional solvent is added slowly to the reactants for recovery of the product. The boiling solvent, already present, heats the incoming solvent to prevent thermal shock to the reactor walls. Upon cooling, the product separates as a slurry in the solvent thereby providing for easy removal from the reactor while limiting the product contact with air and moisture.

The solvent added before cooling the reactor should bring the content of the reactor to about 50% solvent for easy recovery. This amount, however, is not a requirement of the invention since it is only necessary that the added amount, when required, be sufficient to allow for facile recovery. The solubility of the dimer in the solvent is low at room temperature and the product crystallizes upon cooling and is removed as a slurry. Without the addition of more solvent, the product would solidify in the reactor when cooled and would stall the agitator. The disclosed process presents an alternative to the prior art where the product would have to be removed while molten or otherwise breaking the reactor to release the product after cooling. In the slurry form, exposure to air and moisture during handling is reduced and charging to the next processing step is simplified.

EXAMPLE 1

310 grams of ethylthionophosphonic dichloride (EPTD) was reacted with hydrogen sulfide by charging the ethylthionophosphonic dichloride to a 3 neck 2 liter reaction flask affixed with a reflux condenser to which was attached a caustic scrubber. The reactor was flushed with nitrogen. The ethylthionophosphonic dichloride charge was then heated to reflux temperatures of from about 150° to 160° C. Hydrogen sulfide was then passed beneath the surface of the dichloride at rates in the range of 0.8 to 2 grams per minute until the reaction was completed (until no HCl is detected). During this process the reaction temperature was maintained in the range of from 160° to 220° C. Solids were formed on the walls of the reactor, above the liquid level, by the end of the reaction. The reactor exhaust opening was nearly closed by the needle-like crystals. The reaction took about 8 hours.

After stopping the H$_2$S flow, the reactor was cooled above the melting point of the disulfide product to 155° C. and 180 gms of room temperature toluene were slowly added through the condenser. The toluene boiled when contacting the hot liquid, and the vapors were condensed and returned to the reactor by the condenser. A heavy slurry formed when the temperature reached 105° C. An additional 95 gms of toluene were added and the reactor was reheated to 120° C. A thick slurry formed at 103° C. The product was a pinkish solid dispersed in a brown liquid.

EXAMPLE 2

411.8 grams of ethylthionophosphonic dichloride (EPTD) was charged to the reaction flask used in Example 1 with 60.6 grams of toluene. The reactor was sparged with nitrogen during the process. As in the previous reaction hydrogen sulfide was passed beneath the surface of the dichloride at varying rates in the range of 0.3 to 1.0 gm per minute until no HCl was being formed. The temperature at the time of the addition of the H$_2$S was about 150° C. rising to about 200° C. by the end of the reaction. The reaction took 16.5 hours. No solids formed in the vapor zone during this reaction. The refluxing toluene continually washed any product formed back into the reactor, and no solids were visible in the reactor.

After stopping the H$_2$S addition at a temperature of 203° C., 90 gms of toluene was added slowly through the condenser. The incoming toluene was heated before contact with the reaction liquid due to contact with refluxing toluene. Solids began to form at 118° C. Additional toluene was added to form a thinner slurry.

EXAMPLE 3

To a two liter 3-neck flask as used in Example I was added a packed column. The condenser above the column was used to return the refluxing EPTD and toluene to the column during reflux. To the flask was charged 423.3 grams of ethylthionophosphonic dichloride (EPTD) and 22.5 grams of toluene. H$_2$S was charged to the reactor (as previously indicated in the prior examples) when the temperature was 150° C. and the temperature during reaction varied between 150°-165° C. The reaction was continued and, upon conclusion (after 9½ hours), 267 grams of toluene was added to the reactor. The product obtained was a slurried liquid.

EXAMPLE 4

A plant scale run was made based upon the previous example by charging 16.5 lbs. (7.48 kgs) of toluene to a reactor and 110.5 lbs. (50.0 kgs) of EPTD. The reactor was heated to 220° F. (104.4° C.) before charging H$_2$S. Then 137.5 lbs. (62.4 kg) of H$_2$S was sparged into the reactor over 26½ hours while the temperature was between 150° C. and 165° C. After completion of the reaction 90 lbs. of toluene was slowly added to the column while the reactor was at 165° C. The toluene already present in the reactor was refluxing in the column and the incoming toluene was thereby heated to near its boiling point. This avoided thermal shock to the glass lined steel reactor. The maximum allowable temperature difference for this vessel was 100° C. No solids were present in the column at any time. The product slurry was drained from the reactor.

What is claimed is:

1. A process for producing a disulfide dimer of hydrocarbylthiophosphonic dichloride which comprises the reaction of hydrocarbylthiophosphonic dichloride of the formula

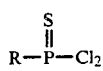

wherein R is a hydrocarbyl radical free of aliphatic unsaturation and hydrogen sulfide and wherein a solvent is used for preparing and recovering the product.

2. The process of claim 1 further comprising utilizing a packed column in the process.

3. The process of claim 1 wherein the solvent utilized is toluene.

4. The process of claim 1 wherein the hydrocarbylthiophosphonic is ethyl thionophosphonic dichloride.

5. The process of claim 1 wherein the disulfide dimer is produced in the form of a slurry.

6. The process of claim 1 wherein from about 1 to 20%, by weight of the total reactants, of solvent is added during the reaction process.

7. The process of claim 1 wherein solvent is added after completion of the reaction to produce a slurried product.

8. The process of claim 1 wherein a sufficient amount of solvent is added during the reaction to maintain a liquid reaction medium.

* * * * *

UNITED STATES PATENT AND TRADEMARK OFFICE
CERTIFICATE OF CORRECTION

PATENT NO. : 4,697,028

DATED : September 29, 1987

INVENTOR(S) : Louis F. Bolzan

It is certified that error appears in the above-identified patent and that said Letters Patent is hereby corrected as shown below:

In column 2, at line 6, the word "toly" should read --- tolyl ---.

In Column 2, the first full paragraph appearing before the first formula should read:

--- The hydrocarbylthionophosphine sulfides of the invention are prepared by reacting hydrogen sulfide with a hydrocarbylthiophosphonic dichloride of the formula ---

In column 4, line 61, the number "50.0" should read --- 50.1 ---.

Signed and Sealed this

Tenth Day of January, 1989

*Attest:*

DONALD J. QUIGG

*Attesting Officer*    *Commissioner of Patents and Trademarks*